United States Patent [19]

Stedronsky et al.

[11] Patent Number: 5,817,303
[45] Date of Patent: Oct. 6, 1998

[54] BONDING TOGETHER TISSUE WITH ADHESIVE CONTAINING POLYFUNCTIONAL CROSSLINKING AGENT AND PROTEIN POLYMER

[75] Inventors: Erwin R. Stedronsky, San Clement; Joseph Cappello, San Diego, both of Calif.

[73] Assignee: Protein Polymer Technologies, Inc., San Diego, Calif.

[21] Appl. No.: 435,641

[22] Filed: May 5, 1995

[51] Int. Cl.$^6$ .............. A61K 31/785; A01N 37/18; C07K 1/00; C12N 11/00
[52] U.S. Cl. ............................ 424/78.02; 106/124.1; 424/78.06; 435/174; 514/2; 530/350; 530/402; 530/810
[58] Field of Search ............................ 435/174, 180; 424/486, 78.02; 514/2; 106/124, 124.1; 530/300, 350, 402, 810

[56] References Cited

U.S. PATENT DOCUMENTS

| | | | |
|---|---|---|---|
| 4,187,852 | 2/1980 | Urry | 128/334 R |
| 4,589,882 | 5/1986 | Urry | 623/11 |
| 4,898,926 | 2/1990 | Urry | 528/328 |
| 5,064,430 | 11/1991 | Urry | 623/1 |
| 5,243,038 | 9/1993 | Ferrari et al. | 536/23.1 |
| 5,292,362 | 3/1994 | Bass et al. | 106/124 |
| 5,336,256 | 8/1994 | Urry | 623/1 |
| 5,374,431 | 12/1994 | Pang et al. | 424/486 |
| 5,496,712 | 3/1996 | Cappello et al. | 435/69.1 |
| 5,514,581 | 5/1996 | Ferrari et al. | 435/252.33 |

FOREIGN PATENT DOCUMENTS

| | | |
|---|---|---|
| 4334396 | 11/1992 | Japan . |
| 93/04711 | 3/1993 | WIPO . |
| 94/01508 | 2/1994 | WIPO . |
| 95/05396 | 2/1995 | WIPO . |

OTHER PUBLICATIONS

Kaleem et al., "Collagen–Based Bioadhesive Varnacle Cement Mimic", Die Angewandte Makromolekulare Chemie (1987), 155:31–43.

*Primary Examiner*—David M. Naff
*Attorney, Agent, or Firm*—Richard F. Trecartin; Mark T. Kresnak; Flehr Hohbach Test Albritton and Herbert

[57] ABSTRACT

Proteinaceous polymers having repetitive units from naturally occurring structural proteins are employed as backbones for functionalities for crosslinking to provide strongly adherent tissue adhesives and sealants. Particularly, block copolymers having repeating units of elastin and fibroin are employed having lysine substitutions in spaced apart units, where the amino group can be crosslinked using difunctional crosslinking agents. The protein polymer contains at least 40 weight percent of repetitive units of 3 to 15 amino acids of at least one naturally occurring protein and in at least two units an amino acid is substituted by an amino acid containing a functional group capable of reacting with a crosslinking agent to form a strongly adherent adhesive composition for bonding together separated tissue or for sealing tissue defects. A preferred adhesive composition contains glutaraldehyde or polymethylene diisocyanate and a protein block copolymer of at least 30 kD containing at least 70 weight percent of repetitive units of Gly-Ala-Gly-Ala-Gly-Ser and Gly-Val-Gly-Val-Pro, where in at least two units an amino acid is substituted with lysine and the copolymer has a lysine equivalent weight in the range of 1 to 20 kD. The protein polymer is produced by recombinant DNA technology, and a kit can be formed containing the crosslinking agent and protein polymer.

23 Claims, No Drawings

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
        Gly  Ala  Gly  Ala  Gly  Ser
        1                 5
```

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
        Gly  Val  Gly  Val  Pro
        1                 5
```

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
        Ala  Lys  Leu  Xaa  Leu  Ala  Glu
        1                 5
```

( 2 ) INFORMATION FOR SEQ ID NO:4:

( i ) SEQUENCE CHARACTERISTICS:
        ( A ) LENGTH: 64 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Gly  Ala  Gly  Ala  Gly  Ser  Gly  Ala  Gly  Ala  Gly  Ser  Gly  Ala  Gly  Ala
1                 5                              10                           15
Gly  Ser  Gly  Ala  Gly  Ala  Gly  Ser  Gly  Val  Gly  Val  Pro  Gly  Val  Gly
                  20                             25                           30
Val  Pro  Gly  Val  Gly  Val  Pro  Gly  Val  Gly  Val  Pro  Gly  Lys  Gly  Val
                  35                             40                           45
Pro  Gly  Val  Gly  Val  Pro  Gly  Val  Gly  Val  Pro  Gly  Val  Gly  Val  Pro
                  50                             55                           60
```

( 2 ) INFORMATION FOR SEQ ID NO:5:

( i ) SEQUENCE CHARACTERISTICS:
        ( A ) LENGTH: 64 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Gly  Ala  Gly  Ala  Gly  Ser  Gly  Ala  Gly  Ala  Gly  Ser  Gly  Ala  Gly  Ala
1                 5                              10                           15
Gly  Ser  Gly  Ala  Gly  Ala  Gly  Ser  Gly  Val  Gly  Val  Pro  Gly  Val  Gly
                  20                             25                           30
Val  Pro  Gly  Val  Gly  Val  Pro  Gly  Val  Gly  Val  Pro  Gly  Glu  Gly  Val
```

```
                    35                           40                           45
        Pro Gly Val Gly Val Pro Gly Val Gly Val Pro Gly Val Gly Val Pro
            50                           55                           60
```

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
CTGGAGCGGG TGCCTGCATG TACATCCGAG T                                       31
```

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
ACTCGGATGT ACATGCAGGC ACCCGCTCCA GAGCC                                   35
```

(2) INFORMATION FOR SEQ ID NO:8:

(i) SEQUENCE CHARACTERISTICS:
        (A) LENGTH: 192 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

```
GGTGCCGGTT CTGGAGCTGG CGCGGGCTCT GGAGTAGGTG TGCCAGGTGT AGGAGTTCCG        60
GGTGTAGGCG TTCCGGGAGT TGGTGTACCT GGAGTGGGTG TTCCAGGCGT AGGTGTGCCC       120
GGGGTAGGAG TACCAGGGGT AGGCGTGCCT GGAGCGGGTG CTGGTAGCGG CGCAGGCGCG       180
GGCTCTGGAG CG                                                          192
```

(2) INFORMATION FOR SEQ ID NO:9:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
        Gly Ala Gly Ser Gly Ala Gly Ala Gly Ser Gly Val Gly Val Gly
        1               5                   10                  15
        Val Gly Val Gly Pro Gly Val Gly Val Pro Gly Val Gly Val Pro Gly
                        20                  25                  30
        Val Gly Val Pro Gly Val Gly Val Pro Gly Val Gly Val Pro Gly Val
                    35                  40                  45
        Gly Val Pro Gly Ala Gly Ala Gly Ser Gly Ala Gly Ala Gly Ser Gly
                50                  55                  60
```

```
        Ala
        65
```

( 2 ) INFORMATION FOR SEQ ID NO:10:

( i ) SEQUENCE CHARACTERISTICS:
        ( A ) LENGTH: 201 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

```
ATGGCAGCGA  AAGGGGACCG  GGCTCTGGTG  TTGGAGTGCC  AGGTGTCGGT  GTTCCGGGTG      60
TAGGCGTTCC  GGGAGTTGGT  GTACCTGGAA  AGGTGTTCCG  GGGGTAGGTG  TGCCGGGCGT     120
TGGAGTACCA  GGTGTAGGCG  TCCCGGGAGC  GGGTGCTGGT  AGCGGCGCAG  GCGCGGGCTC     180
TTTCCGCTAA  AGTCCTGCCG  T                                                  201
```

( 2 ) INFORMATION FOR SEQ ID NO:11:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
AAGAAGGAGA  TATCATATGG  CAGCGAAAGG  GGACC                                   35
```

( 2 ) INFORMATION FOR SEQ ID NO:12:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

```
CGCAGATCTT  TAAATTACGG  CAGGACTTTA  GCGGAAA                                 37
```

( 2 ) INFORMATION FOR SEQ ID NO:13:

( i ) SEQUENCE CHARACTERISTICS:
        ( A ) LENGTH: 192 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:13:

```
GGTGCCGGTT  CTGGAGCTGG  CGCGGGCTCT  GGTGTTGGAG  TGCCAGGTGT  CGGTGTTCCG      60
GGTGTAGGCG  TTCCGGGAGT  TGGTGTACCT  GGAAAAGGTG  TTCCGGGGGT  AGGTGTGCCG     120
GGCGTTGGAG  TACCAGGTGT  AGGCGTCCCG  GGAGCGGGTG  CTGGTAGCGG  CGCAGGCGCG     180
GGCTCTGGAG  CG                                                             192
```

( 2 ) INFORMATION FOR SEQ ID NO:14:

( i ) SEQUENCE CHARACTERISTICS:

(A) LENGTH: 64 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:14:

| Gly | Ala | Gly | Ser | Gly | Ala | Gly | Ala | Gly | Ser | Gly | Val | Gly | Val | Pro | Gly |
| 1 | | | | 5 | | | | | 10 | | | | | 15 | |

| Val | Gly | Val | Pro | Gly | Val | Gly | Val | Pro | Gly | Val | Gly | Val | Pro | Gly | Lys |
| | | | 20 | | | | | 25 | | | | | 30 | | |

| Gly | Val | Pro | Gly | Val | Gly | Val | Pro | Gly | Val | Gly | Val | Pro | Gly | Val | Gly |
| | | 35 | | | | | 40 | | | | | 45 | | | |

| Val | Pro | Gly | Ala | Gly | Ala | Gly | Ser | Gly | Ala | Gly | Ala | Gly | Ser | Gly | Ala |
| | | 50 | | | | 55 | | | | | 60 | | | | |

(2) INFORMATION FOR SEQ ID NO:15:

(i) SEQUENCE CHARACTERISTICS:
    (A) LENGTH: 884 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:15:

| Met | Asp | Pro | Val | Val | Leu | Gln | Arg | Arg | Asp | Trp | Glu | Asn | Pro | Gly | Val |
| 1 | | | | 5 | | | | | 10 | | | | | 15 | |

| Thr | Gln | Leu | Asn | Arg | Leu | Ala | Ala | His | Pro | Pro | Phe | Ala | Ser | Asp | Pro |
| | | | 20 | | | | | 25 | | | | | 30 | | |

| Met | Gly | Ala | Gly | Ser | Gly | Ala | Gly | Ala | Gly | Ser | Gly | Val | Gly | Val | Pro |
| | | | 35 | | | | | 40 | | | | | 45 | | |

| Gly | Val | Gly | Val | Pro | Gly | Val | Gly | Val | Pro | Gly | Val | Gly | Val | Pro | Gly |
| | | | 50 | | | | | 55 | | | | | 60 | | |

| Lys | Gly | Val | Pro | Gly | Val | Gly | Val | Pro | Gly | Val | Gly | Val | Pro | Gly | Val |
| 65 | | | | | 70 | | | | | 75 | | | | | 80 |

| Gly | Val | Pro | Gly | Ala | Gly | Ala | Gly | Ser | Gly | Ala | Gly | Ala | Gly | Ser | Gly |
| | | | | 85 | | | | | 90 | | | | | 95 | |

| Ala | Gly | Ala | Gly | Ser | Gly | Ala | Gly | Ala | Gly | Ser | Gly | Val | Gly | Val | Pro |
| | | | 100 | | | | | 105 | | | | | 110 | | |

| Gly | Val | Gly | Val | Pro | Gly | Val | Gly | Val | Pro | Gly | Val | Gly | Val | Pro | Gly |
| | | | 115 | | | | | 120 | | | | | 125 | | |

| Lys | Gly | Val | Pro | Gly | Val | Gly | Val | Pro | Gly | Val | Gly | Val | Pro | Gly | Val |
| | | 130 | | | | | 135 | | | | | 140 | | | |

| Gly | Val | Pro | Gly | Ala | Gly | Ala | Gly | Ser | Gly | Ala | Gly | Ala | Gly | Ser | Gly |
| 145 | | | | | 150 | | | | | 155 | | | | | 160 |

| Ala | Gly | Ala | Gly | Ser | Gly | Ala | Gly | Ala | Gly | Ser | Gly | Val | Gly | Val | Pro |
| | | | | 165 | | | | | 170 | | | | | 175 | |

| Gly | Val | Gly | Val | Pro | Gly | Val | Gly | Val | Pro | Gly | Val | Gly | Val | Pro | Gly |
| | | | | 180 | | | | | 185 | | | | | 190 | |

| Lys | Gly | Val | Pro | Gly | Val | Gly | Val | Pro | Gly | Val | Gly | Val | Pro | Gly | Val |
| | | | 195 | | | | | 200 | | | | | 205 | | |

| Gly | Val | Pro | Gly | Ala | Gly | Ala | Gly | Ser | Gly | Ala | Gly | Ala | Gly | Ser | Gly |
| | | 210 | | | | | 215 | | | | | 220 | | | |

| Ala | Gly | Ala | Gly | Ser | Gly | Ala | Gly | Ala | Gly | Ser | Gly | Val | Gly | Val | Pro |
| 225 | | | | | 230 | | | | | 235 | | | | | 240 |

| Gly | Val | Gly | Val | Pro | Gly | Val | Gly | Val | Pro | Gly | Val | Gly | Val | Pro | Gly |

|   |   |   |   |   | 245 |   |   |   |   | 250 |   |   |   |   | 255 |   |
|---|---|---|---|---|---|---|---|---|---|---|---|---|---|---|---|---|

Lys Gly Val Pro Gly Val Gly Val Pro Gly Val Gly Val Pro Gly Val
                260                 265                 270

Gly Val Pro Gly Ala Gly Ala Gly Ser Gly Ala Gly Ala Gly Ser Gly
            275                 280                 285

Ala Gly Ala Gly Ser Gly Ala Gly Ala Gly Ser Gly Val Gly Val Pro
            290                 295                 300

Gly Val Gly Val Pro Gly Val Gly Val Pro Gly Val Gly Val Pro Gly
305                 310                 315                 320

Lys Gly Val Pro Gly Val Gly Val Pro Gly Val Gly Val Pro Gly Val
                325                 330                 335

Gly Val Pro Gly Ala Gly Ala Gly Ser Gly Ala Gly Ala Gly Ser Gly
            340                 345                 350

Ala Gly Ala Gly Ser Gly Ala Gly Ala Gly Ser Gly Val Gly Val Pro
            355                 360                 365

Gly Val Gly Val Pro Gly Val Gly Val Pro Gly Val Gly Val Pro Gly
            370                 375                 380

Lys Gly Val Pro Gly Val Gly Val Pro Gly Val Gly Val Pro Gly Val
385                 390                 395                 400

Gly Val Pro Gly Ala Gly Ala Gly Ser Gly Ala Gly Ala Gly Ser Gly
                405                 410                 415

Ala Gly Ala Gly Ser Gly Ala Gly Ala Gly Ser Gly Val Gly Val Pro
            420                 425                 430

Gly Val Gly Val Pro Gly Val Gly Val Pro Gly Val Gly Val Pro Gly
            435                 440                 445

Lys Gly Val Pro Gly Val Gly Val Pro Gly Val Gly Val Pro Gly Val
            450                 455                 460

Gly Val Pro Gly Ala Gly Ala Gly Ser Gly Ala Gly Ala Gly Ser Gly
465                 470                 475                 480

Ala Gly Ala Gly Ser Gly Ala Gly Ala Gly Ser Gly Val Gly Val Pro
                485                 490                 495

Gly Val Gly Val Pro Gly Val Gly Val Pro Gly Val Gly Val Pro Gly
            500                 505                 510

Lys Gly Val Pro Gly Val Gly Val Pro Gly Val Gly Val Pro Gly Val
            515                 520                 525

Gly Val Pro Gly Ala Gly Ala Gly Ser Gly Ala Gly Ala Gly Ser Gly
530                 535                 540

Ala Gly Ala Gly Ser Gly Ala Gly Ala Gly Ser Gly Val Gly Val Pro
545                 550                 555                 560

Gly Val Gly Val Pro Gly Val Gly Val Pro Gly Val Gly Val Pro Gly
            565                 570                 575

Lys Gly Val Pro Gly Val Gly Val Pro Gly Val Gly Val Pro Gly Val
            580                 585                 590

Gly Val Pro Gly Ala Gly Ala Gly Ser Gly Ala Gly Ala Gly Ser Gly
            595                 600                 605

Ala Gly Ala Gly Ser Gly Ala Gly Ala Gly Ser Gly Val Gly Val Pro
            610                 615                 620

Gly Val Gly Val Pro Gly Val Gly Val Pro Gly Val Gly Val Pro Gly
625                 630                 635                 640

Lys Gly Val Pro Gly Val Gly Val Pro Gly Val Gly Val Pro Gly Val
            645                 650                 655

Gly Val Pro Gly Ala Gly Ala Gly Ser Gly Ala Gly Ala Gly Ser Gly
            660                 665                 670

```
Ala  Gly  Ala  Gly  Ser  Gly  Ala  Gly  Ala  Gly  Ser  Gly  Val  Gly  Val  Pro
          675                      680                      685
Gly  Val  Gly  Val  Pro  Gly  Val  Gly  Val  Pro  Gly  Val  Gly  Val  Pro  Gly
     690                      695                      700
Lys  Gly  Val  Pro  Gly  Val  Gly  Val  Pro  Gly  Val  Gly  Val  Pro  Gly  Val
705                      710                      715                           720
Gly  Val  Pro  Gly  Ala  Gly  Ala  Gly  Ser  Gly  Ala  Gly  Ala  Gly  Ser  Gly
                    725                      730                      735
Ala  Gly  Ala  Gly  Ser  Gly  Ala  Gly  Ala  Gly  Ser  Gly  Val  Gly  Val  Pro
               740                      745                      750
Gly  Val  Gly  Val  Pro  Gly  Val  Gly  Val  Pro  Gly  Val  Gly  Val  Pro  Gly
          755                      760                      765
Lys  Gly  Val  Pro  Gly  Val  Gly  Val  Pro  Gly  Val  Gly  Val  Pro  Gly  Val
     770                      775                      780
Gly  Val  Pro  Gly  Ala  Gly  Ala  Gly  Ser  Gly  Ala  Gly  Ala  Gly  Ser  Gly
785                      790                      795                           800
Ala  Gly  Ala  Gly  Ser  Gly  Ala  Gly  Ala  Gly  Ser  Gly  Val  Gly  Val  Pro
               805                      810                      815
Gly  Val  Gly  Val  Pro  Gly  Val  Gly  Val  Pro  Gly  Val  Gly  Val  Pro  Gly
               820                      825                      830
Lys  Gly  Val  Pro  Gly  Val  Gly  Val  Pro  Gly  Val  Gly  Val  Pro  Gly  Val
               835                      840                      845
Gly  Val  Pro  Gly  Ala  Gly  Ala  Gly  Ser  Gly  Ala  Gly  Ala  Gly  Ser  Gly
     850                      855                      860
Ala  Gly  Ala  Met  Asp  Pro  Gly  Arg  Tyr  Gln  Asp  Leu  Arg  Ser  His  His
865                      870                      875                           880
His  His  His  His
```

BONDING TOGETHER TISSUE WITH ADHESIVE CONTAINING POLYFUNCTIONAL CROSSLINKING AGENT AND PROTEIN POLYMER

TECHNICAL FIELD

The field of this invention is physiologically acceptable compositions for use as tissue adhesives and sealants.

BACKGROUND

In many situations, there is a need to bond separated tissues. Sutures and staples are effective and well established wound closure devices. However, there are surgical procedures where classical repair procedures are unsatisfactory, limited to highly trained specialists (e.g. microsurgery), or not applicable due to tissue or organ fragility, inaccessibility (e.g. endoscopy procedures), or fluid loss, including capillary "weeping". Tissue adhesives and sealants have been developed to meet these needs. They may be used to seal or reinforce wounds that have been sutured or stapled, as well as finding independent use. The leading commercial products are fibrin glues and cyanoacrylates. However, both products have significant limitations which have prevented their widespread use.

Cyanoacrylates are mainly used for cutaneous wound closure in facial and reconstructive surgery. The appeal of cyanoacrylates is their speed of bonding, which is almost immediate, and its great bond strength. However, its speed of bonding can be a disadvantage, since glued tissue must be cut again in order to reshape it to the desired conformation. Additionally, it can only be used on dry substrates since its mode of action is through a mechanical interlock, limiting its use as a sealant, and it is relatively inflexible compared to surrounding tissue. Cyanoacrylates are also known to be toxic to some tissues and although it is not considered to be biodegradable, potential degradation products are suspected to be carcinogenic.

Fibrin glues comprising blood-derived fibrinogen, factor XIII and thrombin function primarily as a sealant and hemostat and have been used in many different surgical procedures within the body. They have been shown to be non-toxic, biocompatible and biodegradable. They are able to control excessive bleeding and decrease fibrosis. However, tissues bonded with fibrin cannot be subjected to even moderate tensile stress without rupturing the bond. It takes about three to ten minutes for an initial bond to develop, but requires about 30 minutes to several hours for full strength to develop. Depending upon the application, the product may also resorb too quickly. Use of recombinantly produced fibrinogen, factor XIII, thrombin and related components (e.g. fibrin, activated factor XIII) has not been demonstrated to improve the setting time or strength of fibrin glues. Fibrin glues derived from heterologous, human and animal, serum may provoke undesirable immune responses, and expose the patient to the potential risk of viral infection. Autologous fibrin glues may be impractical to obtain and use and may compromise patient safety.

There is, therefore, substantial interest in developing products which have the biocompatibility of fibrin glues, but which set more quickly and have enhanced strength. These products should be readily available, desirably from other than natural sources, be easily administered and capable of resorption over time.

Relevant Literature

Tissue adhesives are described in: Tissue Adhesives in Surgery, Matsumoto, T., Medical Examination Publishing Co., Inc. 1972 and Sierra, D. H., J. Biomat. App. 7:309–352, 1993. Methods of preparation of protein polymers having blocks of repetitive units are described in U.S. Pat. No. 5,243,038 and EPA 89.913054.3.

SUMMARY OF THE INVENTION

Polymeric compositions and methods for their use are provided, where the polymeric compositions are capable of in situ chemical crosslinking to provide strong adherent bonds to tissue. The compositions can be used to bond separated tissue in the presence of blood to provide a stable, flexible, resorbable bond, as well as other applications.

DESCRIPTION OF THE SPECIFIC EMBODIMENTS

The subject compositions comprise high molecular weight recombinant polymers having one or a combination of repeating units related to naturally occurring structural proteins. Of particular interest are the repeating units of fibroin, elastin, collagen, and keratin, particularly collagen, and combinations of fibroin and elastin. The polymers have functional groups which can be chemically crosslinked under physiological conditions with physiologically acceptable crosslinkers, so as to form strongly adherent bonds to tissue to maintain separated tissue in a contiguous spacial relationship. The subject compositions may also be employed as sealants, where the compositions may serve to fill a defect void in tissue. The functionalities may be all the same or combinations of functionalities and may include the functionalities of naturally occurring amino acids, such as amino, e.g. lysine, carboxyl, e.g. aspartate and glutamate, guanidine, e.g. arginine, hydroxyl, e.g. serine and threonine, and thiol, e.g. cysteine. Preferably, the functionality is amino.

The polymers will have molecular weights of at least about 15 kD, generally at least about 30 kD, preferably at least about 50 kD and usually not more than 250 kD, more usually not more than about 150 kD. The polymers will have at least two functionalities, more usually at least about four functionalities, generally having an equivalent weight per functionality in the range of about 1 kD to 20 kD, more usually in the range of about 3 kD to 15 kD. If desired, one may use mixtures of polymers, where the polymers have combinations of functionalities or have different functionalities present e.g. carboxyl and amino, thiol and aldehydo, hydroxyl and amino, etc. Thus, depending upon the functionalities and the crosslinking agent, one can form amides, imines, esters, ethers, urethanes, thioethers, disulfides, and the like.

The individual units in the polymer may be selected from fibroin, Gly-Ala-Gly-Ala-Gly (SEQ ID NO:01); elastin, Gly-Val-Gly-Val-Pro (SEQ ID NO:02); collagen GXX, where at least 10% of the X's are proline and not more than 45%, and keratin, Ala-Lys-Leu-Lys/Glu-Leu-Ala-Glu (SEQ ID NO:3), where the desired functionality may be substituted for one of the amino acids of an individual unit. Of particular interest are copolymers, either block or random, preferably block, where the ratio of elastin units to fibroin units is in the range of 16-1:1, preferably 8-1:1, where blocks may have different ratios. Normally, in block copolymers, each block will have at least two units and not more than about 32 units, usually not more than about 24 units. By substituting an amino acid in the unit with an amino acid having the appropriate functionality, one can provide for the appropriate number of functionalities present in the polymer.

The individual amino acid repeat units will have from about 3 to 30 amino acids, usually 3 to 25 amino acids, more usually 3 to 15 amino acids, frequently about 3 to 9 amino acids. At least 40 weight %, usually at least 50 weight %, more usually at least 70 weight %, of the protein polymer will be composed of segments of repetitive units containing at least 2 identical contiguous repetitive units.

While for the most part, the polymers of the subject invention will have the active functionality of a naturally occurring amino acid in the chain of the polymer, if desired, pendent groups may be employed to provide the desired functionalities. For example, carboxyl groups may be reacted with polyamines so as to exchange a carboxyl functionality for a single amino or plurality of amino groups. An amino group may be substituted with a polycarboxylic acid, so that the amino group will be replaced with a plurality of carboxylic groups. A thiol may be replaced with an aldehyde, by reaction with an aldehydic olefin, e.g. acrolein, so as to provide for an aldehyde functionality. Other functionalities which may be introduced, if desired, include phosphate esters, activated olefins, e.g. maleimido, thioisocyanato, and the like. The functionalities may be greatly varied from those which naturally occur to provide opportunities for crosslinking. In some instances, this may be desirable to increase the number of functionalities per unit molecular weight, while not increasing the number of functionalities along the chain, for replacing one functionality with another, e.g. thiol with aldehyde, allowing for greater variation in the choice of crosslinking agent.

The crosslinking agent will normally be difunctional, where the functionalities may be the same or different, although higher functionality may be present, usually not exceeding four functionalities. Depending upon the particular functionalities available on the polymers, various crosslinking agents may be employed. The crosslinking agents will usually be at least about three carbon atoms and not more than about 20 carbon atoms, generally ranging from about 3 to 16 carbon atoms, more usually from about 3 to 10 carbon atoms. The chain joining the two functionalities will be at least one atom and not more than about 12 atoms, usually not more than about 10 atoms, preferably not more than about 8 atoms, where the atoms may be carbon, oxygen, nitrogen, sulfur, phosphorous, or the like. The linking group may be aliphatically saturated or unsaturated, preferably aliphatic, and may include such functionalities as oxy, amide, thioether, amino, and phosphorous ester.

Various reactive functionalities may be employed, such as aldehyde, isocyanate, mixed carboxylic acid anhydride, e.g. ethoxycarbonyl anhydride, activated olefin, activated halo, amino, and the like. By appropriate choice of the functionalities on the protein polymer, and the crosslinking agent, rate of reaction and degree of crosslinking can be controlled.

Various crosslinking agents may be employed, particularly those which have been used previously and have been found to be physiologically acceptable. Crosslinking agents which may be used include dialdehydes, such as glutaraldehyde, activated olefin aldehydes, such as acrolein, diisocyanates such as, tetramethylene diisocyanate, hexamethylene diisocyanate, octamethylene diisocyanate, acid anhydrides, such as succinic acid dianhydride, ethylene diamine tetraacetic acid dianhydride, diamines, such as hexamethylene diamine, cyclo(L-lysyl-L-lysine) etc. The crosslinking agents will usually be commercially available or may be readily synthesized in accordance with conventional ways.

The subject compositions may be prepared prior to the use of the adhesive by combining the protein polymer and the crosslinking agent, where one or both may have extenders. The two compositions may be readily mixed in accordance with conventional ways, for example, using syringes which can inject the ingredients into a central reactor and the mixture mixed by drawing the mixture back into the syringes and moving the mixture back and forth. Usually, the polymer will be available as a dispersion or solution, generally the concentration of the protein polymer being in the range of about 50 mg to 1 g/ml, more usually from about 100 to 800 mg/ml. The ratio of crosslinking agent to polymer will vary widely, depending upon the crosslinking agent, the number of functionalities present on the polymer, the desired rate of curing, and the like. Generally, the weight ratio of polymer to crosslinking agent will be at least about 1:1 and not greater than about 100:1, usually not greater than about 50:1, more usually not greater than about 30:1, generally being in the range of about 2 to 20:1.

If desired, various extenders or extending agents may be used, particularly naturally occurring proteins. Such extenders will usually not exceed 50 weight percent of the composition, generally not exceeding about 20 weight percent, more usually not exceeding about 10 weight percent. Extenders which may be employed include, but are not limited to: synthetic polymers, both addition and condensation polymers, such as polylactides, polyglycolides, polyanhydrides, polyorthoesters, polyvinyl compounds, polyolefins, polyacrylates, polyethylene glycol, polyesters, polyvinyl alcohol, polyethers, copolymers and derivatives thereof; and naturally occurring polymers, such as proteins, including collagen, fibrinogen, fibronectin, laminin, keratin, chitosan, heparin, dextran, alginates, cellulose, glycosoaminoglycans, hyaluronic acid, derivatives thereof, and the like. The extenders may modulate the setting time and provide for desirable physical or physiological properties of the adhesive.

Based on the lap shear tensile strength test described in the experimental section, within 30 min, usually within 15 min, more usually within 5 min, the lap shear tensile strength will be at least 200, preferably at least about 250, more preferably at least about 300, usually not exceeding about 1500, more usually not exceeding about 1200 $g/cm^2$.

The subject compositions may be applied to the tissue in any convenient way, for example by using a syringe, catheter, cannula, manually applying the composition, spraying or the like.

In addition to their use as adhesives, the subject compositions may be used to seal or fill defects, e.g. voids or holes, in tissue, and therefore find use as sealants. Thus, the compositions may serve to stop or staunch the flow of fluid, e.g. blood, through ruptured vessels, e.g. arteries, veins, capillaries and the like. In using the subject compositions as sealants, the composition will be applied, as described above, at the site of the defect, whereby it will set and seal the defect.

The subject compositions may also find use in the formation of articles of manufacture, by themselves or in combination with other materials. In one application, articles may be produced for use internally to a mammalian host, where there is an interest in biocompatibility, reabsorption rate, ability to vascularize, tissue adhesive and/or bonding capability, and the like. Various articles can be prepared, such as gels, films, threads, coatings, formed objects such as pins and screws, or injectable compositions which are flowable, where the injectable composition may set up and bond or seal tissues, form a depot for a drug, or be a filler, coating or the like. The formed objects may be prepared in accordance with conventional ways, such as molding, extrusion, precipitation from a solvent, solvent evaporation, and the like. The flowable depot can be obtained by using a molecular dispersion, fine particles in a medium saturated with a polymer, using a melt, where the melting temperature may be achieved by adding physiologically acceptable additives, and the like.

The articles may find use in a variety of situations associated with the implantation of the article into a mammalian host or the application of the article to the surface of a mammalian host, e.g. wound healing, burn dressing, etc. Those situations, where the performance of the articles may be retained for a predetermined time and replaced by natural materials through natural processes, desirably employ materials which will be resorbed after having fulfilled their function in maintaining their role until the natural process has reestablished a natural structure. Thus, the compositions may find use in holding tissue together, covering tissue, encapsulating cells for organs, providing a coating that cells can invade and replace the composition with natural composition, e.g., bone, soft tissues and the like.

To enhance the rate of curing of the polymeric composition, the composition may be partially prepolymerized. When prepolymerized, the polymer will usually have at least about 5% of the total number of crosslinks and not more than about 75% of the total number of crosslinks, as compared to completion of the crosslinking action. The number of crosslinks should allow the resulting product to be workable and provide sufficient time prior to set up for it to be manipulated and used.

The subject compositions may also be used as depots to provide for a relatively uniform release of a physiologically active product, e.g., a drug. The drug may be mixed with a subject composition at an appropriate concentration prior to crosslinking. As the crosslinked polymer is degraded, the drug will be released due to diffusion as well as erosion of the external surface of the depot. By controlling the form or shape of the depot, the degree of crosslinking, the concentration of the drug and the like, a physiologically therapeutic level of the drug may be maintained over extended periods of time. The period required for absorption can be as short as 0.5 day and may exceed 4, 6 or 8 weeks or more, depending upon the particular composition.

The protein polymer compositions may be prepared in accordance with conventional ways. See, for example, U.S. Pat. No. 5,243,038, which disclosure is herein incorporated by reference. Briefly, sequences may be synthesized comprising a plurality of repeating units, where complementary sequences result in dsDNA having overhangs. A series of dsDNA molecules may be prepared and stepwise introduced into a cloning vector as the gene for the protein is constructed. A monomer can be obtained in this way, which may be sequenced to ensure that there have been no changes in the sequence, followed by multimerization of the monomer, cloning and expression. For further details, see the above indicated patent.

The following examples are offered by way of illustration and not by way of limitation.

EXPERIMENTAL

EXAMPLE 1

Methods

The construction of synthetic DNA and its use in large polypeptide synthesis is described in U.S. Pat. No. 5,243,038; PCT/US89/05016 and PCT/US92/09485, the disclosures of which are herein incorporated by reference. Modifications to these methods and additional methods used are described below.

1. Use of filters and columns for DNA Purification
  A. Ultrafree®-Probind filter unit ("Probind", Millipore): the DNA containing solution was applied to the filter unit and spun at 12,000 RPM for 30 seconds in a Sorvall Microspin 24S.
  B. Microcon-30 filter (Amicon): the DNA containing solution was washed by applying to the filter and exchanging twice with $H_2O$ by spinning at 12,000 RPM for 6 min in a microfuge.
  C. Bio-Spin 6 column ("Bio-Spin", BioRad): Salts and glycerol were removed from the DNA solution by applying to the column, previously equilibrated in TEAB (triethyl ammonium bicarbonate pH 7.0), and spinning in a Sorvall RC5B centrifuge using an HB4 rotor at 2,500 RPM for 4 min.

2. Phosphatase treatment of DNA

Phosphatase treatment of DNA was also performed by resuspending ethanol precipitated DNA from the restriction enzyme digest in 20 mM Tris-HCl pH 8.0, 10 mM $MgCl_2$ to a final DNA concentration of 20 $\mu$g/ml. Shrimp Alkaline Phosphatase (SAP) was added at 2 U/$\mu$g of DNA and the mixture was incubated at 37° C. for one hour, heat inactivated for 20 minutes at 65° C. and then passed through a Probind filter and subsequently a Bio-Spin column.

3. Preparative agarose get electrophoresis

For agarose ligation, the buffer used was 1x TAE (50 mM Tris-acetate, pH 7.8).

4. Agarose DNA Ligation

The agarose was melted at 65° C., the temperature was then lowered to 37° C. and ligation buffer (5x=100 mM Tris-HCl, pH 7.5, 50 mM $MgCl_2$, 50 mM DTT, 1 mM ATP) was added; the tube was then placed at room temperature and ligase was added (1000 units T4 DNA ligase (NEB)). The reaction volume was usually 50 $\mu$l. The reaction was incubated at 15° C. for 16–18 hrs.

5. Agarose DNA purification using an Ultrafree®-MC Filter Unit

This procedure can be used for agarose slices up to 400 $\mu$l in size. After agarose gel electrophoresis, the DNA is visualized by ethidium bromide staining and the agarose block containing the DNA band of interest is excised. The agarose is then frozen at −20° C. for 1 hour, then quickly thawed at 37° C. for 5 minutes. The agarose is then thoroughly macerated. The pieces are then transferred into the sample cup of the filter unit and spun at 5,000 xg in a standard microfuge for 20 minutes. The agarose is then resuspended in 200 $\mu$l of Tris-EDTA, or other buffer, and incubated at room temperature for 30 minutes to allow for elution of additional DNA from the gel. The mixture is then centrifuged for an additional 20 minutes at 10,000 RPM. The DNA is, at this point, in the filtrate tube separated from the agarose fragments and ready for subsequent DNA manipulations.

6. Preparation of antibody to artificially synthesized peptides

The same procedures were used as described in U.S. Pat. No. 5,243,038, PCT/US89/05016 and PCT/US92/09485.

7. Immunoblotting of proteins in gels

An alternative to the $^{125}$I-Protein A detection method was used. This method relied on a chemiluminescent signal activated by horseradish peroxidase HRP). The chemiluminescent reagents are readily available from several suppliers such as Amersham and DuPont NEN. The western blot was prepared and blocked with BLOTTO. A number of methods were used to introduce the HRP reporter enzyme including, for example, a hapten/anti-hapten-HRP, a biotinylated antibody/streptavidin-HRP, a secondary reporter such as a goat or mouse anti-rabbit IgG-biotinylated/streptavidin-HRP, or a goat or mouse-anti rabbit IgG-HRP. These reagents were bought from different sources such as BioRad or Amersham and occasionally biotinylated antibodies were prepared in our laboratory using Biotin NHS from Vector Laboratories, Burlingame, Calif. (Cat. #SP-1200) following the procedure accompanying the product. The following is an example of a procedure used to detect the expression of protein polymers.

The blot was placed in 15 ml of BLOTTO solution containing biotinylated goat anti-rabbit IgG (BioRad) diluted in BLOTTO (1:7500) and gently agitated for 2 hrs at room temperature. The filter was then washed for 30 minutes with 3 changes of TSA (50 mM Tris-HCl pH 7.4, 0.9% NaCl, 0.2% sodium azide) and then for 5 min each in TBS with 0.1% TWEEN®20. The blot was then incubated for 20 minutes at room temperature with gentle rotation, in 20 ml of TBS (100 mM Tris Base, 150 mM NaCl, pH 7.5) HRP-Streptavidin (Amersham) diluted 1:1000 in TBS with 0.1% Tween 20. The blot was then washed three times for 5 minutes each in TBS with 0.3% Tween 20 and then three times for 5 minutes each in TBS with 0.1% Tween 20. The blot was then incubated for 1 minute with gentle agitation in 12 ml of development solutions #1 an #2 (Amersham) equally mixed. The blot was removed from the development solution and autoradiographed.

8. Protein expression analysis

An overnight culture which had been grown at 30° C. was used to inoculate 50 ml of LB media contained in a 250 ml flask. Kanamycin was added at a final concentration of 50 $\mu$g per ml and the culture was incubated with agitation (200 rpm) at 30° C. When the culture reached an $OD_{600}$ of 0.8, 40 ml were transferred to a new flask prewarmed at 42° C. and incubated at the same temperature for approximately 2 hours. The cultures (30° and 42°) were chilled on ice and $OD_{600}$ was taken. Cells were collected by centrifugation and then divided in 1.0 $OD_{600}$ aliquots and used to perform western analysis using the appropriate antibodies.

9. Amino acid analysis

Amino acid derivatives were analyzed by reverse phase HPLC using a Waters 600E system.

10. Peptide Synthesis

Synthetic peptides were also prepared on a Rainin/Protein Technologies PS3 FMOC peptide synthesizer. Both the synthesis and cleavage were accomplished using the methods supplied by the manufacturer in the instrument manual.

11. In vitro DNA synthesis

The β-cyanoethyl phosphoramidites, controlled-pore glass columns and all synthesis reagents were obtained from Applied Biosystems, Foster City, Calif. Synthetic oligonucleotides were prepared by the phosphite triester method with an Applied Biosystems Model 381A DNA synthesizer using a 10-fold excess of protected phosphoramidites and 0.2 $\mu$mole of nucleotide bound to the synthesis support column. The chemistries used for synthesis are the standard protocols recommended for use with the synthesizer and have been described (Matteucci et al., *J. Amer. Chem. Soc.*, 103:3185–3319 (1981)). Deprotection and cleavage of the oligomers from the solid support were performed according to standard procedures as provided by Applied Biosystems. The repetitive yield of the synthesis as measured by the optical density of the removed protecting group as recommended by Applied Biosystems was greater than 97.5%.

The crude oligonucleotide mixture was purified by preparative gel electrophoresis as described by the Applied Biosystems protocols in Evaluating and Isolating Synthetic Oligonucleotides, 1992 (Formerly: User Bulletin 13, 1987). The acrylamide gel concentration varied from 10 to 20% depending upon the length of the oligomer. If necessary, the purified oligomer was identified by UV shadowing, excised from the gel and extracted by the crush and soak procedure (Smith, *Methods in Enzymology*, 65:371–379 (1980)).

For DNA synthesis of oligonucleotides longer then 100 bases, the synthesis cycle was changed from the protocol recommended by Applied Biosystems for the 381A DNA synthesizer. All the reagents used were fresh. All the reagents were supplied by Applied Biosystems except for the acetonitrile (Burdick and Jackson Cat#017-4 with water content less then 0.001%) and the 2000 Å pore size column (Glen Research). Due to the length of the oligo, interrupt pauses had to be inserted during the synthesis to allow changing the reagent bottles that emptied during synthesis. This interrupt pause was done at the cycle entry step and the pause was kept as short as possible. The washes after detritylation by TCA, through the beginning of each synthesis cycle, were increased from about 2x to 3x over the recommended time. The time allocated for the capping was also increased to limit truncated failure sequences. After the synthesis the deprotection was done at 55° C. for 6 hours. After desalting the synthesized DNA was amplified using PCR.

12. Sequencing of DNA

Storage and analysis of data utilized software from DNA Strider, DNA Inspection IIe or DNAid for Apple Macintosh personal computer.

13. Dideoxy DNA sequencing of double stranded plasmid DNA

As described in U.S. Pat. No. 5,243,038, plasmid DNA was prepared on a small scale. Primers were synthesized using a DNA synthesizer and were annealed to the plasmid DNA following the procedure described for M13 sequencing. The sequencing reactions were done using Sequenase (United States Biochemicals) and the conditions were as recommended by the supplier. All sequences were run on polyacrylamide gels.

14. PCR Amplification

The PCR reaction was performed in a 100 $\mu$l volume in a Perkin Elmer thin-walled Gene Amp™ reaction tube. Approximately 1 $\mu$M of each primer DNA was added to 1x PCR buffer (supplied by Perkin Elmer as 10x solution), 200 $\mu$M of each dNT, 5U AmpliTaq, and several concentrations of the target DNA. Amplification was performed in a Perkin Elmer DNA Thermal cycler model 480 for 30 cycles with the following step cycles of 12 min each: 95° C., 62° C., and 72° C. Aliquots from the different reactions were analyzed by agarose gel electrophoresis using 1.5% low melting point agarose in 0.5x TA buffer. The reaction mixtures that gave the desired band were pooled and spun through a Probind filter to remove the AmpliTaq enzyme, then a Microcon-30 filter and a Bio-Spin column. The DNA was then concentrated in vacuo.

15. Fermentation conditions

The fermentors used for the expression of protein polymers were usually a 15 l MBR, 10 l working volume, or a 13 l Braun Biostat E, 8.5 l working volume. The choice of the fermentor and its size is not critical. Any media used for the growth of *E. coli* can be used. The nitrogen source ranged from NZAmine to inorganic salts and the carbon source generally used was glycerol or glucose. All fermentations were done with the appropriate selection conditions imposed by the plasmid requirements (e.g. kanamycin, ampicillin, etc.). The fermentation method used to express protein polymers in *E. coli* was the fed-batch method. This is the preferred method for the fermentation of recombinant organisms even if other methods can be used.

The fed-batch method exploits the stage of cell growth where the organisms make a transition from exponential to stationary phase. This transition is often the result of either depletion of an essential nutrient or accumulation of a metabolic byproduct. When the transition is the result of nutrient depletion, the addition of nutrients to the system causes cell division to continue. One or more essential nutrients can incrementally be added to the fermentation vessel during the run, with the net volume increasing during the fermentation process. The result is a controlled growth rate where biomass and expression levels can be optimized. When the cell number in the culture has reached or is approaching a maximum, protein polymer production is induced by providing an appropriate physical or chemical signal, depending upon the expression system used. Production will then continue until the accumulated product reaches maximum levels (Fiestchko, J., and Ritch, T., *Chem. Eng. Commun.* 1986, 45:229–240. Seo, J. H.; Bailey, J. E., Biotechnol. Bioeng. 1986, 28:1590–1594.

EXAMPLE 2
Construction of SELP8K and SELP8E

Polymers were prepared designated SELP8K and SELP8E, which are characterized by having functional groups for cross-linking. The construction of these polymers is described below starting from the previous gene monomer, SELPO (see U.S. Pat. No. 5,243,038, pSY1298). SELP8K and SELP8E amino acid monomer sequence design:
SELP8K MONOMER, (Gly-Ala-Gly-Ala-Gly-Ser)$_4$ (Gly-Val-Gly-Val-Pro)$_4$ Gly-Lys-Gly-Val-Pro (Gly-Val-Gly-Val-Pro)$_3$ (GVGVP)$_3$ (SEQ ID NO:04)
SELP8E MONOMER (Gly-Ala-Gly-Ala-Gly-Ser)$_4$ (Gly-Val-Gly-Val-Pro)$_4$ Gly-Glu-Gly-Val-Pro (Gly-Val-Gly-Val-Pro)$_3$ (GVGVP)$_3$ (SEQ ID NO:05)
SELP8 construction Plasmid pSY1378 (see U.S. Pat. No. 5,243,038) was digested with BanI REN, purified using agarose gel electrophoresis followed by NACS column, and the DNA was then ethanol precipitated in 2.5 M ammonium acetate and ligated with pPT0134 (See PCT/US92/09485) previously digested with FokI REN, phenol/chloroform extracted and ethanol precipitated.

The products of the ligation mixture were transformed into *E. coli* strain HB101. Plasmid DNA from transformants was purified and analyzed by digestion using NruI and XmnI RENs. Plasmid pPT0255 containing the desired restriction pattern was obtained and was used for subsequent constructions.

Plasmid DNA pPT0255 was treated with Cfr10I REN followed by RNAse. The digestion fragments were separated by agarose gel electrophoresis, the DNA was excised and self-ligated. The products of the ligation mixture were transformed into *E. coli* strain HB101. Plasmid DNA from transformants was purified and analyzed by digestion using NaeI and StuI RENs. Plasmid pPT0267 containing the desired deletion was used for subsequent constructions.

Two oligonucleotide strands as shown in Table 1 were synthesized and purified as described in Example 1.

TABLE 1

| 5'- CTGGAGCGGGTGCCTGCATGTACATCCGAGT -3 (SEQ ID NO:06) |
| 3'- CCGAGACCTCGCCCACGGACGTACATGTAGGCTCA -5' (SEQ ID NO:07) |

The two oligonucleotide strands were annealed and ligated with the DNA of plasmid pPT0267 which had been previously digested with BanII and ScaI RENs, and purified by agarose gel electrophoresis followed by NACS column.

The products of this ligation reaction were transformed into *E. coli* strain HB101. Plasmid DNA from transformants was purified and digested with DraI. Plasmid DNA from two clones that gave the correct digestion pattern was sequenced. One plasmid DNA, designated pPT0287, was found to be correct and chosen for further constructions.

Plasmid DNA pSY1298 (see U.S. Pat. No. 5,243,038) was digested with BanII REN, and the SELPO gene fragment was purified by agarose gel electrophoresis followed by NACS and then ligated to pPT0287 digested with BanII. The enzyme was then removed using phenol/chloroform extraction and ethanol precipitation.

The products of the ligation mixture were transformed into *E. coli* strain HB101. Plasmid DNA from transformants was purified and analyzed by digestion using DraI REN. Plasmid DNA from the clones showing the correct restriction pattern was further digested with BanII, AhaII and StuI RENs. Plasmid pPT0289 contained the desired SELP8 monomer sequence (see Table 2).

TABLE 2

SELP8 Gene Monomer Sequence

BanI                                                                BanII
GGT GCC GGT TCT GGA GCT GGC GCG GGC TCT GGA GTA GGT GTG CCA GGT
CCA CGG CCA AGA CCT CGA CCG CGC CCG AGA CCT CAT CCA CAC GGT CCA
Gly—Ala—Gly—Ser—Gly—Ala—Gly—Ala—Gly—Ser—Gly—Val—Gly—Val—Pro—Gly
GTA GGA GTT CCG GGT GTA GGC GTT CCG GGA GTT GGT GTA CCT GGA GTG
CAT CCT CAA GGC CCA CAT CCG CAA GGC CCT CAA CCA CAT GGA CCT CAC
Val—Gly—Val—Pro—Gly—Val—Gly—Val—Pro—Gly—Val—Gly—Val—Pro—Gly—Val
                                                  SmaI
GGT GTT CCA GGC GTA GGT GTG CCC GGG GTA GGA GTA CCA GGG GTA GGC
CCA CAA GGT CCG CAT CCA CAC GGG CCC CAT CCT CAT GGT CCC CAT CCG
                                                            BanII
GTC CCT GGA GCG GGT GCT GGT AGC GGC GCA GGC GCG GGC TCT GGA GCG
CAG GGA CCT CGC CCA CGA CCA TCG CCG CGT CCG CGC CCG AGA CCT CGC
Val—Pro—Gly—Ala—Gly—Ala—Gly—Ser—Gly—Ala—Gly—Ala—Gly—Ser—Gly—Ala
(SEQ ID NOS: 08 & 09)

Construction of SELP8K and SELP8E Gene Monomers

One oligonucleotide strand coding for a portion of the SELP8 gene monomer was synthesized with a single base polymorphism at position 90. The use of both adenine and guanidine at this position produced oligonucleotides from a single synthesis that encoded the amino acids lysine and glutamic acid (see Table 3). The synthesis was conducted using an Applied Biosystems DNA synthesizer model 381A and a 2000Å synthesis column supplied by Glen Research. During the synthesis the required interrupt-pauses for bottle changes were minimized. After the synthesis the 202 base DNA fragment was deprotected and cleaved from the column support by treatment in 30% ammonium hydroxide at 55° C. for 6 hrs.

TABLE 3

ATGGCAGCGAAAGGGGACCGGGCTCTGGTGTTGGAGTGCCAGGTGTCGGTGTTCCGGGTGTAGGCGTTC
CGGGAGTTGGTGTACCTGGA(A/G)AAGGTGTTCCGGGGGTAGGTGTGCCGGGCGTTGGAGTACCAGGT
GTAGGCGTCCCGGGAGCGGGTGCTGGTAGCGGCGCAGGCGCGGGCTCTTTCCGCTAAAGTCCTGCCGT-3'
(SEQ ID NO:10)
Two additional DNA strands were used as primers for PCR amplification. The two strands were:
1. 5'-AAGAAGGAGATATCATATGGCAGCGAAAGGGGACC-3' (SEQ ID NO:11)
2. 5'-CGCAGATCTTTAAATTACGGCAGGACTTTAGCGGAAA-3' (SEQ ID NO:12)

The PCR reaction was carried out and the reaction product was purified as described in Example 1.

The DNA was resuspended and digested with BanII REN as described in Example 1. The digested DNA was then separated by low-melting agarose gel electrophoresis and ligated with pPT0289 previously digested with BanII RENs and purified by NACS column. The products of the ligation reaction were transformed into *E. coli* strain HB101. Plasmid DNA from isolated transformants was purified and analyzed by digestion using ApaLI, and EcoNI RENs. Plasmid DNA from the clones showing the correct restriction pattern were further analyzed by digestion using Asp700 REN to distinguish between clones encoding a lysine or glutamic acid at the polymorphic position. Plasmid DNA from clones containing each of the polymorphs was purified and analyzed by DNA sequencing. Plasmid pPT0340 contained the desired SELP8K monomer sequence (see Table 4) and pPT0350 contained the desired SELP8E monomer sequence.

individual transformants was purified and analyzed for increase size due to SELP8K monomer multiple DNA insertion. Several clones were obtained with insert sizes ranging from 200 bp to approximately 7 kb. Clones containing from 6 to 32 repeats, were used for expression of the SELP8K protein polymer (pPT0341, pPT0343, pPT0344, pPT0345 and pPT0347).

SELP8K Expression Analysis

An overnight culture which had been grown at 30° C. was used to inoculate 50 ml of LB media contained in a 250 ml flask. Kanamycin was added at a final concentration of 50 μg per ml and the culture was incubated with agitation (200 rpm) at 30° C. When the culture reached an $OD_{600}$ of 0.8, 40 ml were transferred to a new flask prewarmed at 42° C. and incubated at the same temperature for approximately 2 hours. The cultures (30° and 42°) were chilled on ice and $OD_{600}$ was taken. Cells were collected by centrifugation and divided in 1.0 $OD_{600}$ aliquots and used to perform western analysis using anti-SLP antibody.

TABLE 4

SELP8K Gene Monomer Sequence

BanI                                BanII
GGT GCC GGT TCT GGA GCT GGC GCG GGC TCT GGT GTT GGA GTG CCA GGT
CCA CGG CCA AGA CCT CGA CCG CGC CCG AGA CCA CAA CCT CAC GGT CCA
Gly—Ala—Gly—Ser—Gly—Ala—Gly—Ala—Gly—Ser—Gly—Val—Gly—Val—Pro—Gly
                                                                    EcoNI
GTC GGT GTT CCG GGT GTA GGC GTT CCG GGA GTT GGT GTA CCT GGA AAA
CAG CCA CAA GGC CCA CAT CCG CAA GGC CCT CAA CCA CAT GGA CCT TTT
Val—Gly—Val—Pro—Gly—Val—Gly—Val—Pro—Gly—Val—Gly—Val—Pro—Gly—Lys
GGT GTT CCG GGG GTA GGT GTG CCG GGC GTT GGA GTA CCA GGT GTA GGC
CCA CAA GGC CCC CAT CCA CAC GGC CCG CAA CCT CAT GGT CCA CAT CCG
Gly—Val—Pro—Gly—Val—Gly—Val—Pro—Gly—Val—Gly—Val—Pro—Gly—Val—Gly
    SmaI                            BanII
GTC CCG GGA GCG GGT GCT GGT AGC GGC GCA GGC GCG GGC TCT GGA GCG
CAG GGC CCT CGC CCA CGA CCA TCG CCG CGT CCG CGC CCG AGA CCT CGC
Val—Pro—Gly—Ala—Gly—Ala—Gly—Ser—Gly—Ala—Gly—Ala—Gly—Ser—Gly—Ala
(SEQ ID NO:13&14)

SELP8K Polymer Construction

Plasmid DNA from pPT0340 was digested with BanI REN and the digestion fragments were separated by agarose gel electrophoresis. The SELP8K gene fragment, 192 bp, was excised and purified by NACS column. The purified fragment was ligated with plasmid pPT0317 which had been digested with BanI REN, passed through a Millipore Probind and a Bio-Spin 6 column. The DNA was then treated with shrimp alkaline phosphatase (SAP) as described in Example 1. The products of this ligation reaction were transformed into *E. coli* strain HB101. Transformants were selected for resistance to kanamycin. Plasmid DNA from

*E. coli* strain HB101 containing plasmids pPT0341, pPT0343, pPT0344, pPT0345 and pPT0347 were grown as described above. The proteins produced by these cells were analyzed by Western blot for detection of proteins reactive to SLP antibodies. Each clone produced a strongly reactive band. The apparent molecular weights of the products ranged from approximately 35 kD to greater than 250 kD. Strain pPT0345 produced an SLP antibody reactive band of apparent molecular weight 80,000. The expected amino acid sequence of the SELP8K polymer encoded by plasmid pPT0345 is shown below.

pPT0345  SELP8K  884 AA  MW 69,772
Met—Asp—Pro—Val—Val—Leu—Gln—Arg—Arg—Asp—Trp—Glu—Asn—Pro—Gly—Val—Thr—Gln—Leu—Asn—
Arg—Leu—Ala—Ala—His—Pro—Pro—Phe—Ala—Ser—Asp—Pro—Met—Gly—Ala—Gly—Ser—Gly—Ala—
Gly—Ala—Gly—Ser
[(Gly—Val—Gly—Val—Pro)$_4$Gly—Lys—Gly—Val—Pro(Gly—Val—Gly—Val—
Pro)$_3$(Gly—Ala—Gly—Ala—Gly—Ser)$_4$]$_{12}$
(Gly—Val—Gly—Val—Pro)$_4$Gly—Lys—Gly—Val—Pro(Gly—Val—Gly—Val—
Pro)$_3$(Gly—Ala—Gly—Ala—Gly—Ser)$_2$
Gly—Ala—Gly—Ala—Met—Asp—Pro—Gly—Arg—Tyr—Gln—Asp—Leu—Arg—Ser—His—His—His—
His—His—His (SEQ ID NO:15)

SELP8K Purification

SELP8K was produced in *E. coli* strain pPT0345 by fermentation. The product was purified from the cellular biomass by means of cellular lysis, clearance of insoluble debris by centrifugation, and affinity chromatography. The purified product was analyzed by sodium dodecyl sulfate polyacrylamide gel electrophoresis, immunoreactivity with a polyclonal antisera which reacts with silk-like peptide blocks (SLP antibody), and amino acid analysis. A protein band of apparent molecular weight 80,000 was observed by amido black staining of SDS-PAGE separated and transferred samples and the same band reacted with the SLP antibody on Western blots. As expected, amino acid analysis (shown in Table 5) indicated that the product was enriched for the amino acids glycine (43.7%), alanine (12.3%), serine (5.3%), proline (11.7%), and valine (21.2%). The product also contained 1.5% lysine. The amino acid composition table below shows the correlation between the composition of the purified product and the expected theoretical compositions as deduced from the synthetic gene sequence.

TABLE 5

Amino Acid Analysis of Purified SELP8K

| Amino Acid | pmoles | ACTUAL % composition | THEORETICAL % composition |
|---|---|---|---|
| Ala | 1623.14 | 12.3 | 12.2 |
| Asx | 122.20 | 0.9 | 0.8 |
| Glx | nd | nd | 0.4 |
| Phe | 58.16 | 0.4 | 0.1 |
| Gly | 5759.31 | 43.7 | 41.5 |
| His | 46.75 | 0.4 | 0.8 |
| Ile | 43.87 | 0.3 | 0 |
| Lys | 198.21 | 1.5 | 1.5 |
| Leu | 39.54 | 0.3 | 0.5 |
| Met | 36.01 | 0.3 | 0.3 |
| Pro | 1534.21 | 11.7 | 12.4 |
| Arg | 70.84 | 0.5 | 0.6 |
| Ser | 703.83 | 5.3 | 6.1 |
| Thr | nd | nd | 0.1 |
| val | 2797.47 | 21.2 | 22.4 |
| Tyr | 140.87 | 1.1 | 0.1 | nd = none detected

EXAMPLE 3

Properties Evaluation

Test Procedures

Tiseel Adhesive Systems.

Rat skins were washed with water, blotted dry and cut into strips about 1 cm×4 cm. Adhesive from Tiseel Kit VH (Osterreiches Institute Fur Haemoderivate, GmbH, A-1220, Vienna, Austria) was applied according to the manufacturer's specifications.

Rat Skin Lap Shear Tensile Strength Assay.

Adhesive formulations were tested for their ability to bond skin together using an in vitro rat skin lap shear tensile strength assay. Adhesives were applied to the subcutaneous side of a strip of harvested rat skin. A second skin strip was overlapped in order to produce an approximate bonding surface 1 cm$^2$. A 100 gram weight was applied to the lap joint and the adhesive was allowed to cure, usually at room temperature for a period of 2 hours and wrapped in plastic to prevent desiccation. The lap joint was mounted on an Instron Tensile Tester or similar apparatus and tensile force applied. With the Instron, tensile force was typically applied at a constant strain rate of 2 inches per min. The load at failure was recorded and normalized to the measured area of overlap.

Adhesive Systems with Glutaraldehyde.

Rat skins were washed with water, blotted dry, and cut into strips about 1 cm×4 cm. Glutaraldehyde was distilled, stored frozen and thawed immediately before use. Bovine serum albumin was dissolved according to Goldman's specifications (Goldman, WO94/01508). CLP6 (prepared as described in PCT/US92/09485 using strain pPT0246 (CLP6 referred to as DCP6)) was dissolved at 600 mg/mL in 150 mM HEPES+30 mM NaCl and adjusted to pH 7.5. SELP8K was dissolved at the concentrations indicated in Table 7 in 150 mM HEPES+45 mM NaCl and adjusted to pH 8. The indicated aliquots of the solution of protein was spread over both skins before the addition of the glutaraldehyde solution. The second skin was overlaid, rubbed across the lower skin to distribute the components, adjusted to an overlap area of ca. 1 cm$^2$, covered with plastic wrap to prevent drying, and cured for 2 h at 25° C. under a compressive force of 100 g/cm$^2$.

Adhesive Systems with 1,6-(Diisocyanto)hexane.

Rat skins were washed with water, blotted dry, and cut into strips about 1 cm×4 cm. A solution of SELP8K was made up in the specified buffer at a concentration of ca. 50% w/w. A 1:1 v/v mixture of hexamethylene diisocyanate (HMDI) and Pluronic L-61 surfactant was prepared. A 20 µL aliquot of SELP8K solution was applied to one skin followed by a 2 µL aliquot of the diluted HMDI. The second skin was overlaid, rubbed across the lower skin to mix the components, adjusted to ca. 1 cm$^2$ overlap, covered with plastic wrap to prevent drying, and cured for 2 h at 25° C. under a compressive force of 100 g/cm$^2$.

Results

In order to provide a baseline for subsequent adhesive experiments, ethyl cyanoacrylate and Tiseel fibrin glue were evaluated. These results are reported in the following table.

TABLE 6

Base Case Lap Shear Tensile Strengths

| Reagent | Dose | Tensile Strength g/cm$^2$ |
|---|---|---|
| Normal Saline | not applicable | 13 ± 4 |
| Tiseel Fibrin Glue | 25 mg (?) | 261 ± 51 |
| Ethyl cyanoacrylate | 25 mg | 385 ± 119 |

All data reported are based on at least three test specimens. All test results are based on a two hour cure time.

The subject compositions were compared to the proteinaceous adhesive system described by Goldman (WO94/01508). Ten microliters of glutaraldehyde was added in all cases. The following table indicates the results.

TABLE 7

Lap Shear Tensile Strength of Glutaraldehyde Cured Adhesive Systems

| Reagent | Dose | Tensile Strength g/cm$^2$ |
|---|---|---|
| Ovalbumin + Glutaraldehyde (30μ) 200 mg/mL 10 μL 2.5N | 6 mg/2.5 mg | 50 ± 10 |
| Atelocollagen(denat) + Glutaraldehyde (25 μL) 125 mg/mL 10 μL 2.5N | 3 mg/2.5 mg | 148 ± 47 |
| CLP6 + Glutaraldehyde (40 μL) 600 mg/mL 10 μL 2.5N | 24 mg/2.5 mg | 306 ± 98 |
| CLP6 + Glutaraldehyde (20 μL) 600 mg/mL 10 μL 2.5N | 12 mg/2.5 mg | 171 ± 42 |
| SELPK (30 μL) + Glutaraldehyde | | |
| 600 mg/mL 1.0N | 18 mg/1 mg | 545 ± 153 |
| 300 mg/mL 1.0N | 9 mg/1 mg | 452 ± 54 |
| 300 mg/mL(impure) 1.0N | 9 mg/1 mg | 234 ± 51 |
| 300 mg/mL(impure) 0.1N | 9 mg/0.1 mg | 210 ± 57* |
| 287 mg/mL 2.5N | 7 mg/2.5 mg | 374 ± 90 |
| 100 mg/mL 1.0N | 3 mg/1 mg | 361 ± 47 |
| 100 mg/mL 2.5N | 3 mg/2.5 mg | 274 ± 17 |

*This prepartion of SELPK was known to be impure and is estimated to yield adhesive strength about one-half of that of the more completely purified material.

The data in the above table demonstrate that the subject polymers are able to provide superior adhesive capabilities when used in the glutaraldehyde cured system under conditions comparable to collagen and ovalbumin. Despite the lower number of amino groups available for crosslinking, the SELPK polymer provides the highest tensile strengths in the rat skin lap shear results. The above results demonstrate that significant adhesion can be obtained at even low doses of glutaraldehyde down to 100 μg/cm$^2$. The quality and purity of the glutaraldehyde is known to be critical to obtain good crosslinking (Rujigrok, DeWijn, Boon, J. Matr. Sci. Matr. Med. 5, 80–87 (1994); Whipple, Ruta, J. Org. Chem. 39, 1666–1668 (1974). The glutaraldehyde used in these experiments was distilled, diluted to 2.5N and stored at −20° C. until used.

In the next study, hexamethylene diisocyanate was employed. It was found necessary to add an equal volume of diluent to obtain good adhesion, since the curing was otherwise too fast. The following table indicates the results, where n=12.

TABLE 8

Lap Shear Tensile Strength of HMDI Derived Adhesive System

| Reagent | Dose | Tensile Strength g/cm$^2$ |
|---|---|---|
| SELPK 20 μL × 50% w/w | 10 mg | 585 ± 203 |
| HMDI/L-61 1:1 v/v 2 μL × 50% v/v | 1 mg | |
| Buffer: (100 μL water + 10 μL 1M KHCO$_3$) | | |
| SELPK 20 μL × 50% w/w | 10 mg | 503 ± 21 |
| HMDI/L-61 1:1 v/v 2 μL × 50% v/v | 1 mg | |
| Buffer: (100 μL 50 mM PO$_4$ (pH 6.8) + 5 μL 1M KHCO$_3$) | | |
| SELPK 20 μL × 50% w/w | 10 mg | 451 ± 67 |
| HMDI/L-61 1:1 v/v 2 μL × 50% v/v | 1 mg | |
| Buffer: (100 μL 50 mM PO$_4$ (pH 6.8) + 10 μL 1M KHCO$_3$) | | |
| SELPK 20 μL × 50% w/w | 10 mg | 362 ± 71 |
| HMDI/L-61 1:1 v/v 20 μL × 50% v/v | 1 mg | |
| Buffer: (100 μL 50 mM PO$_4$ (pH 6.8)) | | |

It is evident from the above results, that the subject invention provides for compositions which can set rapidly to provide a contiguous relationship. The subject invention also provides for compositions that are capable of filling voids or holes in tissue. Thus, the subject proteinaceous polymers may be employed as tissue adhesives, providing physiologically compatible compositions which maintain their strength for extended periods of time, while being capable of resorption, as well as sealants, among other uses.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of maintaining separated viable tissue in proximate relationship, said method comprising:
   applying to said separated viable tissue to hold together said tissue when said tissue is in contiguous relationship, a precursor composition comprising a polyfunctional crosslinking agent and a protein polymer comprising at least 40 weight % of repetitive units of from 3 to 15 amino acids of at least one naturally occurring structural protein, where in at least two units an amino acid is substituted by an amino acid which comprises a functional group capable of reacting with said crosslinking agent, whereby said precursor composition sets up to a strongly adherent adhesive composition and said separated viable tissue is held in proximate relationship.

2. A method according to claim 1, wherein said functional group capable of reacting with said crosslinking agent is amino.

3. A method according to claim 1, wherein said functional group capable of reacting with said crosslinking agent is as a result of reacting a naturally occurring amino acid in said protein polymer with a polyfunctional compound without setting up of said composition.

4. A method according to claim 1, wherein said units are selected from the group consisting of Gly-Ala-Gly-Ala-Gly-Ser (SEQ ID NO:01), Gly-Val-Gly-Val-Pro (SEQ ID NO:02) and GXX, wherein X is any amino acid, at least 10% and not more than 45% of X's being proline.

5. A method according to claim 1, wherein said units are Gly-Ala-Gly-Ala-Gly-Ser (SEQ ID NO:01) and Gly-Val-Gly-Val-Pro (SEQ ID NO:02) and wherein both of said units are present to form a block copolymer protein.

6. A method of maintaining separated viable tissue in proximate relationship, said method comprising:
   applying to said separated viable tissue to hold together said tissue when said tissue is in contiguous relationship, a precursor composition comprising a polyfunctional crosslinking agent reactive with amino groups and a protein block copolymer comprising at least 70 weight % of repetitive units of Gly-Ala-Gly-Ala-Gly-Ser (SEQ ID NO:01) and Gly-Val-Gly-Val-Pro (SEQ ID NO:02), where in at least two units an amino acid is substituted with lysine, which lysine reacts with said crosslinking agent, whereby said precursor composition sets up to a strongly adherent adhesive composition and said separated viable tissue is held in proximate relationship.

7. A method according to claim 6, wherein the equivalent weight of said protein per lysine is in the range of 1 to 20 kD.

8. A method according to claim 6, wherein each block of said block copolymer has at least two units and the ratio of Gly-Ala-Gly-Ala-Gly-Ser (SEQ ID NO:01) to Gly-Val-Gly-Val-Pro (SEQ ID NO:02) is in the range of 1:1–16.

9. A method according to claim 6, wherein said crosslinking agent has a plurality of amino reactive groups selected from the group consisting of aldehyde, isocyanate, thioisocyanate and activated carboxy.

10. A method according to claim 9, wherein said reactive group is aldehyde.

11. A method of maintaining separated viable tissue in proximate relationship, said method comprising:

applying to said separated viable tissue to hold together said tissue when said tissue is in contiguous relationship, a precursor composition comprising a polyfunctional crosslinking agent selected from the group consisting of glutaraldehyde and polymethylene diisocyanate and a protein block copolymer of at least 30 kD comprising at least 70 weight % of repetitive units of Gly-Ala-Gly-Ala-Gly-Ser (SEQ ID NO:01) and Gly-Val-Gly-Val-Pro (SEQ ID NO:02), where in at least two units an amino acid is substituted with lysine, said copolymer having a lysine equivalent weight in the range of 3 to 15 kD, whereby said precursor composition sets up to a strongly adherent adhesive composition and said separated viable tissue is held in proximate relationship.

12. A method of sealing a defect in viable tissue, said method comprising:

applying to said defect a precursor composition comprising a polyfunctional crosslinking agent and a protein polymer comprising at least 40 weight % of repetitive units of from 3 to 15 amino acids of at least one naturally occurring structural protein, where in at least two units an amino acid is substituted by an amino acid which comprises a functional group capable of reacting with said crosslinking agent, whereby said precursor composition sets up to a strongly adherent adhesive composition and said defect is sealed.

13. A method according to claim 12, wherein said units are selected from the group consisting of Gly-Ala-Gly-Ala-Gly-Ser (SEQ ID NO:01), Gly-Val-Gly-Val-Pro (SEQ ID NO:02) and GXX, wherein X is any amino acid, at least 10% and not more than 45% of X's being proline.

14. A method according to claim 12, wherein said units are Gly-Ala-Gly-Ala-Gly-Ser (SEQ ID NO:01) and Gly-Val-Gly-Val-Pro (SEQ ID NO:02) and wherein both of said units are present to form a block copolymer protein.

15. A method according to claim 12, wherein said tissue is the wall of a vessel of the cardiovascular system.

16. A method of maintaining separated viable tissue in proximate relationship, said method comprising:

applying to said separated viable tissue to hold together said tissue when said tissue is in contiguous relationship, a precursor composition comprising a polyfunctional crosslinking agent and a protein polymer comprising at least 40 weight % of repetitive units of from 3 to 15 amino acids of at least one naturally occurring structural protein, where said protein polymer comprises at least two amino acids which comprise a functional group capable of reacting with said crosslinking agent, whereby said precursor composition sets up to a strongly adherent adhesive composition and said separated viable tissue is held in proximate relationship.

17. A kit comprising a polyfunctional crosslinking agent and a protein polymer comprising at least 40 weight % of repetitive units of from 3 to 15 amino acids of at least one naturally occurring structural protein, where in at least two units an amino acid is substituted by an amino acid comprising a functional group capable of reacting with said crosslinking agent.

18. A kit according to claim 17, wherein said functional group capable of reacting with said crosslinking agent is amino.

19. A kit according to claim 17, wherein said functional group capable of reacting with said crosslinking agent is as a result of reacting a naturally occurring amino acid in said protein polymer with a polyfunctional compound without setting up of said composition.

20. A kit according to claim 17, wherein said units are selected from the group consisting of Gly-Ala-Gly-Ala-Gly-Ser (SEQ ID NO:01), Gly-Val-Gly-Val-Pro (SEQ ID NO:02) and GXX, wherein X is any amino acid, at least 10% and not more than 45% of X's being proline.

21. A kit according to claim 17, wherein said units are Gly-Ala-Gly-Ala-Gly-Ser (SEQ ID NO:01) and Gly-Val-Gly-Val-Pro (SEQ ID NO:02) and wherein both of said units are present to form a block copolymer protein.

22. A kit according to claim 17, wherein said crosslinking agent has a plurality of reactive groups selected from the group consisting of aldehydo, isocyanate, thioisocyante and activated carboxy.

23. A kit comprising a protein block copolymer of at least 30 kD comprising at least 70 weight % of repetitive units of Gly-Ala-Gly-Ala-Gly-Ser (SEQ ID NO:01) and Gly-Val-Gly-Val-Pro (SEQ ID NO:02), where in at least two units an amino acid is substituted with lysine, said copolymer having a lysine equivalent weight in the range of 1 to 20 kD and a crosslinking agent selected from the group consisting of glutaraldehyde and aliphatic diisocyanates.

\* \* \* \* \*